(12) United States Patent
Wendland

(10) Patent No.: US 9,775,955 B2
(45) Date of Patent: Oct. 3, 2017

(54) NEEDLE SHIELD ASSEMBLY

(75) Inventor: Stefan Wendland, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 755 days.

(21) Appl. No.: 14/233,391

(22) PCT Filed: Jul. 17, 2012

(86) PCT No.: PCT/EP2012/063955
§ 371 (c)(1),
(2), (4) Date: Jan. 17, 2014

(87) PCT Pub. No.: WO2013/011006
PCT Pub. Date: Jan. 24, 2013

(65) Prior Publication Data
US 2014/0228779 A1 Aug. 14, 2014

(30) Foreign Application Priority Data

Jul. 20, 2011 (EP) .................................... 11174605

(51) Int. Cl.
*A61M 5/00* (2006.01)
*A61M 5/32* (2006.01)
*A61M 5/158* (2006.01)
A61M 5/31 (2006.01)

(52) U.S. Cl.
CPC ............. *A61M 5/32* (2013.01); *A61M 5/158* (2013.01); *A61M 5/3202* (2013.01); *A61M 2005/3109* (2013.01)

(58) Field of Classification Search
CPC .......... A61M 2005/3109; A61M 5/158; A61M 5/32; A61M 5/3202; A61M 5/3213; A61M 5/321; A61M 5/3216; A61M 2005/328; A61M 2005/3254; A61B 50/30
USPC ......................................................... 604/263
See application file for complete search history.

(56) References Cited

U.S. PATENT DOCUMENTS

| 4,636,201 A | 1/1987 | Ambrose et al. |
| 4,986,818 A | 1/1991 | Imbert et al. |
| 5,147,325 A | 9/1992 | Mitchell et al. |
| 5,980,495 A | 11/1999 | Heinz et al. |
| 6,229,314 B1 | 5/2001 | Vetter et al. |

(Continued)

FOREIGN PATENT DOCUMENTS

| EP | 0592814 | 9/1993 |
| EP | 1208861 | 5/2002 |

(Continued)

OTHER PUBLICATIONS

International Search Report for Int. App. No. PCT/EP2012/063955, completed Aug. 21, 2012.

*Primary Examiner* — Jason Flick
(74) *Attorney, Agent, or Firm* — Fish & Richardson P.C.

(57) ABSTRACT

Described is a needle shield assembly comprising an inner body adapted to receive a needle and an outer body coupled to the inner body. The inner body comprises a proximal portion having a first outer diameter (D4) and a distal portion having a second outer diameter. The first outer diameter is larger than the second outer diameter. The outer body has a third outer diameter (D3) substantially equal to or less than the first outer diameter.

10 Claims, 4 Drawing Sheets

(56) References Cited

U.S. PATENT DOCUMENTS

| | | | |
|---|---|---|---|
| 6,719,732 B2 * | 4/2004 | Courteix | A61M 5/3202 604/192 |
| 7,771,397 B1 | 8/2010 | Olson | |
| 2004/0116874 A1 | 6/2004 | Lourenco et al. | |
| 2005/0038391 A1 | 2/2005 | Wittland et al. | |
| 2007/0250016 A1 * | 10/2007 | Pech | A61M 5/3202 604/198 |
| 2009/0287158 A1 | 11/2009 | Hund et al. | |

FOREIGN PATENT DOCUMENTS

| | | |
|---|---|---|
| FR | 2777787 | 4/1998 |
| JP | H10 1998-305098 | 11/1998 |
| JP | 2000354627 | 12/2000 |
| JP | 2009-514634 | 4/2009 |
| WO | 02/11799 | 2/2002 |
| WO | 2009/081133 | 7/2009 |

* cited by examiner

NEEDLE SHIELD ASSEMBLY

CROSS REFERENCE TO RELATED APPLICATIONS

The present application is a U.S. National Phase Application pursuant to 35 U.S.C. §371 of International Application No. PCT/EP2012/063955 filed Jul. 17, 2012, which claims priority to European Patent Application No. 11174605.3 filed Jul. 20, 2011. The entire disclosure contents of these applications are herewith incorporated by reference into the present application.

TECHNICAL FIELD

The invention relates to a needle shield assembly adapted to be placed on a needle of a medicament delivery device.

BACKGROUND

Conventional medicament delivery devices utilize a needle to administer a medicament by injection. For example, a conventional syringe has a needle coupled to a barrel containing the medicament, and the medicament is forced through the needle during the injection. Typically, the needle is protected by a rubber sheath. However, as shown in FIG. 5, the rubber sheath can be subjected to external forces which cause the rubber sheath, and hence the needle, to bend, rendering the syringe unusable. As shown in FIG. 6, a prior solution to preventing the rubber sheath from bending has been to encase the rubber sheath in a plastic cover. However, the conventional plastic covers, as shown in FIG. 6, are bulky and have a large diameter (relative to the rubber sheath), such that packaging of the syringes and/or use of the syringes in an injection device (e.g., an auto-injector) is sub-optimal, given the space required to accommodate the plastic cover.

Conventional needle shielding assemblies are discussed in U.S. Pat. No. 4,636,201 A1, U.S. Pat. No. 5,147,325, US 2007/250016 A1, U.S. Pat. No. 6,229,314 B1, U.S. Pat. No. 4,986,818, and US 2004/116874 A.

However, there remains a need for a needle shield assembly that protects the needle and allows for various uses of the medicament delivery device.

SUMMARY

It is an object of the present invention to provide a needle shield assembly which is mountable on a needle.

In an exemplary embodiment, a needle shield assembly comprises an inner body adapted to receive a needle and an outer body coupled to the inner body. The inner body comprises a proximal portion having a first outer diameter and a distal portion having a second outer diameter. The first outer diameter is larger than the second outer diameter. The outer body has a third outer diameter substantially equal to or less than the first outer diameter. The distal portion of the inner body may be adapted to frictionally engage the needle. The proximal portion of the inner body may be adapted to engage a portion of a medicament delivery device to which the needle is attached.

In an exemplary embodiment, the inner body is constructed of a first material and the outer body is constructed of a second material different from the first material. The first material may be a rubber and the second material may be a plastic or a harder rubber than the rubber of the first material.

In an exemplary embodiment, an inner surface of the outer body includes one or more projections which engage one or more notches on an outer surface of the inner body. In another exemplary embodiment, an outer surface of the inner body includes one or more projections which engage one or more notches on an inner surface of the outer body. The projections may include a first set of projections having a first geometry and a second set of projections having a second geometry.

In an exemplary embodiment, the distal portion of the inner body includes a cap portion having a fourth outer diameter substantially equal to the first outer diameter. A distal end of the outer body may abut the cap portion, and a proximal end of the outer body may abut the proximal portion of the inner body. The cap portion may be one of an annular projection, a partial annular projection, and one or more radial projections.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus, are not limited of the present invention, and wherein.

Corresponding parts are marked with the same reference symbols in all figures.

DETAILED DESCRIPTION

Figure 1:
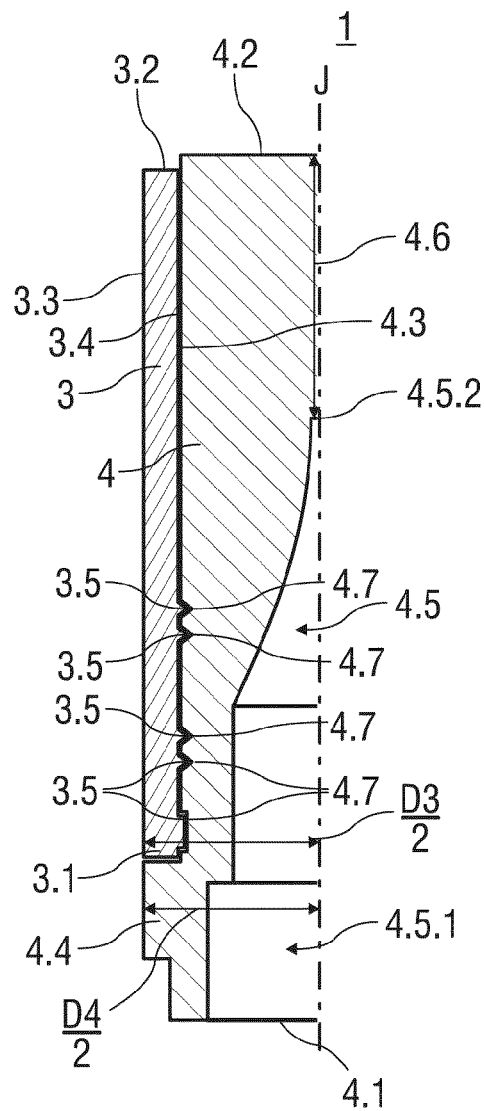
FIG. 1 shows a cross-sectional view of an exemplary embodiment of a needle shield assembly according to the present invention.
Figure 2:
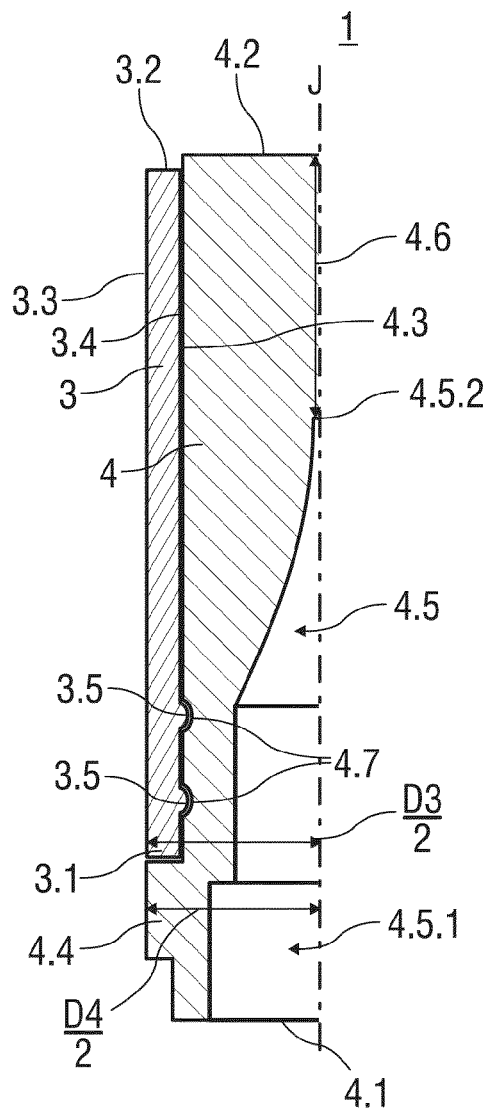
FIG. 2 shows a cross-sectional view of another exemplary embodiment of a needle shield assembly according to the present invention.
Figure 3:
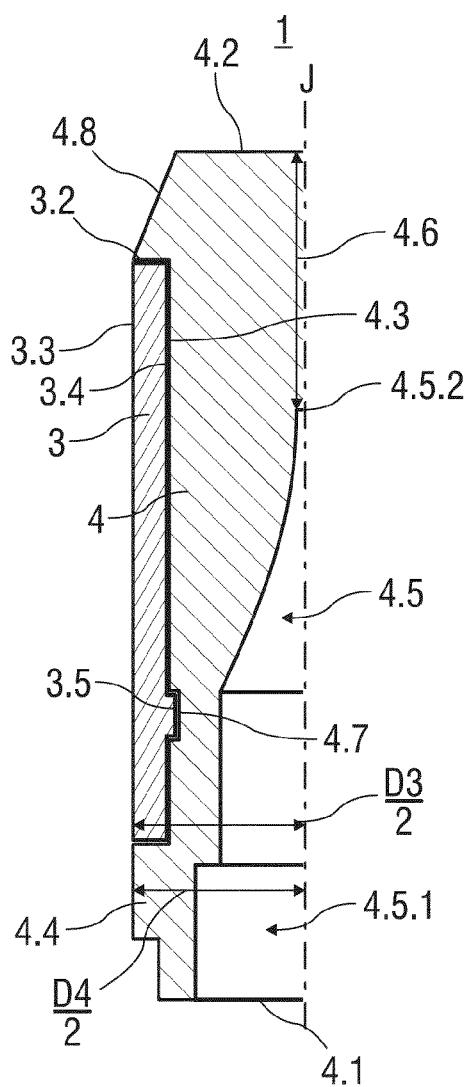
FIG. 3 shows a cross-sectional view of another exemplary embodiment of a needle shield assembly according to the present invention.

FIGS. 1 to 3 show a needle shield assembly 1 in three exemplary embodiments according to the present invention. The needle shield assembly 1 is adapted to be removably mounted to a medicament delivery device 2, e.g., a syringe. Those of skill in the art will understand that the needle shield assembly 1 may be removably mounted on any medical device which includes a needle, e.g., a safety syringe, a needle hub assembly, a biopsy needle, an IV needle, an ablation needle, a suture needle, etc.

As shown in FIG. 1, an exemplary embodiment of a needle shield assembly 1 includes an outer body 3 coupled to an inner body 4. The inner body 4 is adapted to couple to the delivery device 2, including a distal portion adapted to cover a needle 2.1 on the delivery device 2. The inner body 4 also includes a proximal portion adapted to engage and optionally cover a portion of a distal end of the delivery device 2 to which the needle 2.1 is attached. In an exemplary embodiment, the inner body 4 is constructed of a first material (e.g., a soft, thermoplastic elastomer), and the outer body 3 is constructed of a second material (e.g., a plastic, a synthetic or semi-synthetic organic solid as for example polypropylene or polyethylene, a hard rubber).

In an exemplary embodiment, the inner body 4 has a generally cylindrical outer surface 4.3 and includes a proximal end 4.1 and a distal end 4.2. A cavity 4.5 formed in the inner body 4 is adapted to receive the needle 2.1 and a portion of a distal end of the delivery device 2. In an exemplary embodiment, a cavity tip 4.5.1 is sized and shaped to receive the needle 2.1, and a cavity mouth 4.5.2 is sized and shaped to receive a portion of the distal end of the delivery device 2. In an exemplary embodiment, the inner body 4 maintains a frictional engagement to the needle 2.1 and/or the portion of the distal end of the delivery device 2. Those of skill in the art will understand that various modifications may be made to the inner body 4 without departing from the spirit of the invention. For example, the inner body 4 may have a non-circular cross section.

Adjacent the proximal end 4.1 may be a shoulder 4.4. In an exemplary embodiment, the shoulder 4.4 is formed as an annulus around the outer surface 4.3 of the inner body 4. At the shoulder 4.4, the inner body 4 may have a first outer diameter of D4, and at a distal portion 4.6, the inner body 4 may have a second outer diameter, which is smaller than the first diameter.

In an exemplary embodiment, the outer body 3 has a generally cylindrical shape and includes a proximal end 3.1 with an opening adapted to receive the inner body 4. A distal end 3.2 of the outer body 3 may include a cover to enclose the distal end 4.1 of the inner body 4, or the distal end 3.2 of the outer body 3 may be open (as shown in the exemplary embodiment in FIG. 1). The outer body 3 includes an outer surface 3.3 and an inner surface 3.4.

In an exemplary embodiment, the inner surface 3.4 surrounds a cavity which is adapted to receive the inner body 4, and an inner diameter of the outer body 3 is substantially equal to the second outer diameter of the inner body 4. Thus, the outer body 3 may maintain a frictional engagement with the inner body 4. A third outer diameter D3 of the outer body 3 is substantially equal to the first outer diameter D4 of the inner body 4. In another exemplary embodiment, an adhesive and/or welding may be use to couple the outer body 3 to the inner body 4.

In another exemplary embodiment, as shown in FIG. 1, one or more projections 3.5 may be formed on the inner surface 3.4 of the outer body 3. The projections 3.5 may be adapted to engage one or more notches 4.7 formed on the outer surface 4.3 of the inner body 4. Those of skill in the art will understand that the projections 3.5 may be formed on the inner body 4 and the notches 4.7 may be formed on the outer body 3, or that the inner body 4 or outer body 3 may include alternating projections and notches. The engagement of the projections 3.5 and the notches 4.7 may prevent axial movement and/or rotation of the outer body 3 relative to the inner body 4.

In the exemplary embodiment shown in FIG. 1, the projections 3.5 and the notches 4.7 may include a first set of projections having a first geometry and a second set of projections having a second geometry. The first geometry (e.g., triangular, pyramidal, conical, etc.) may be different from the second geometry (e.g., cubical). In another exemplary embodiment, as shown in FIG. 2, the projections 3.5 and the notches 4.7 may be semi-spherical. Those of skill in the art will understand that any shape may be chosen for the projection 3.5 and the corresponding (but inverted) shape may be utilized for the notch 4.7. Those of skill in the art will understand that exemplary embodiments may have the same number of projections and notches or differing numbers of projections and notches.

FIG. 3 shows another exemplary embodiment of a needle shield assembly 1 according to the present invention. In this exemplary embodiment, the distal end 4.2 of the inner body 4 includes a cap portion 4.8. A diameter of the cap portion 4.8 is equal to the first outer diameter D4 of the inner body 4 at the shoulder 4.4. The outer body 3 may be coupled to a portion of the outer surface 4.3 of the inner body 3. The proximal end 3.1 of the outer body may abut the shoulder 4.4, and the distal end 3.2 may abut the cap portion 4.8. The outer body 3 and the inner body 4 may include at least one projection 5 and at least one notch 4.7. Those of skill in the art will understand that, in other exemplary embodiments, the cap portion 4.8 may be an annular projection formed on the distal end 4.2 of the inner body 4 or at some point along the length of the inner body 4, distal of the shoulder 4.4. In another exemplary embodiment, the cap portion 4.8 may be a partial annular projection (e.g., an arc) or one or more radial projections formed on the distal end 4.2 of the inner body 4 or at some point along the length of the inner body 4, distal of the shoulder 4.4.

Figure 7:
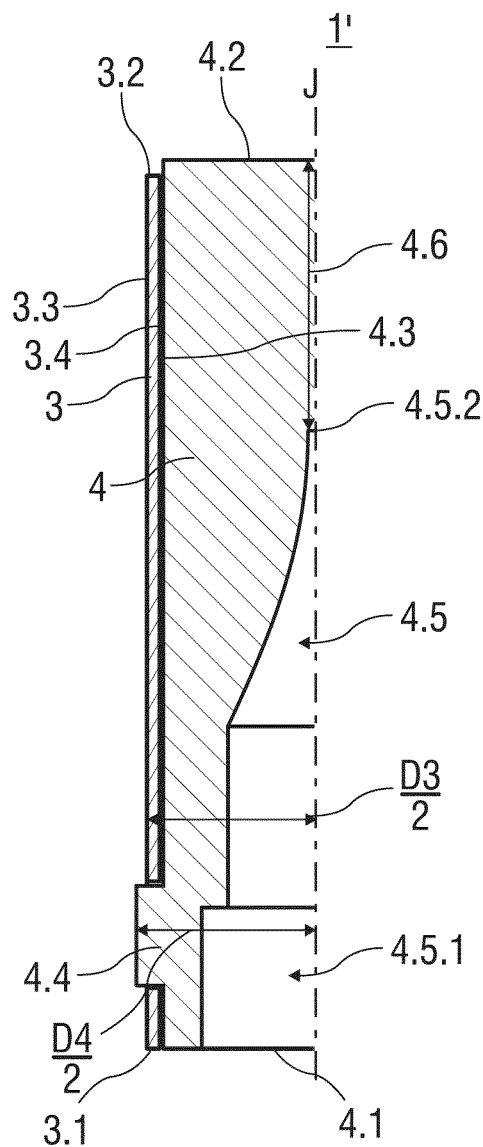
FIG. 7 shows a cross-sectional view of another exemplary embodiment of a needle shield assembly according to the present invention.

FIG. 7 shows another exemplary embodiment of a needle shield assembly 1 according to the present invention. In this exemplary embodiment, an outer body 3 includes an inner surface 3.4 surrounding a cavity which is adapted to receive an inner body 4. An inner diameter of the outer body 3 is substantially equal to the second outer diameter of the inner body 4. Thus, the outer body 3 may maintain a frictional engagement with the inner body 4. A third outer diameter D3 of the outer body 3 may be less than the first outer diameter D4 of the inner body 4 but greater than the second outer diameter of the inner body 4. In this exemplary embodiment, the outer body 3 may also include a portion which surrounds the inner body 4 on a portion proximal of the shoulder 4.4. In another exemplary embodiment, an adhesive and/or welding may be use to couple the outer body 3 to the inner body 4.

Those of skill in the art will understand the outer body 3 may be coupled to the inner body 4 before or after the inner body 4 is coupled to the delivery device 2.

In an exemplary embodiment, the outer body 4 may have one or more apertures which may decrease the amount of material necessary to manufacture the outer body 4.

In an exemplary embodiment, a gripping surface (not illustrated) may be located on the outer surface 3.3 of the outer body 3 for facilitating manipulation of the needle shield assembly 1.

Figure 4:
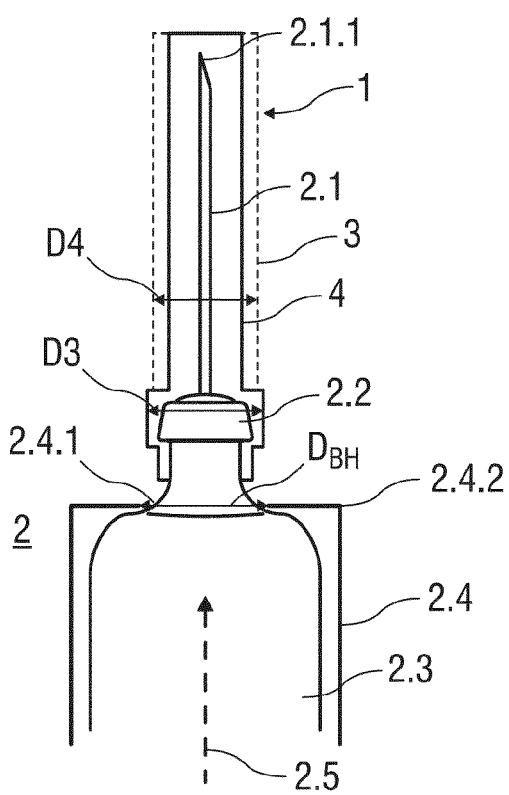
FIG. 4 shows a cross-sectional view of an exemplary embodiment of a medicament delivery device according to the present invention.
Figure 5:
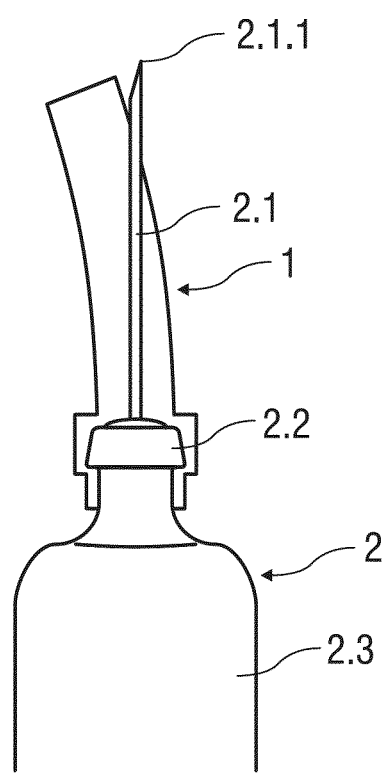
FIG. 5 shows a cross-sectional view of a prior art needle shield assembly.
Figure 6:
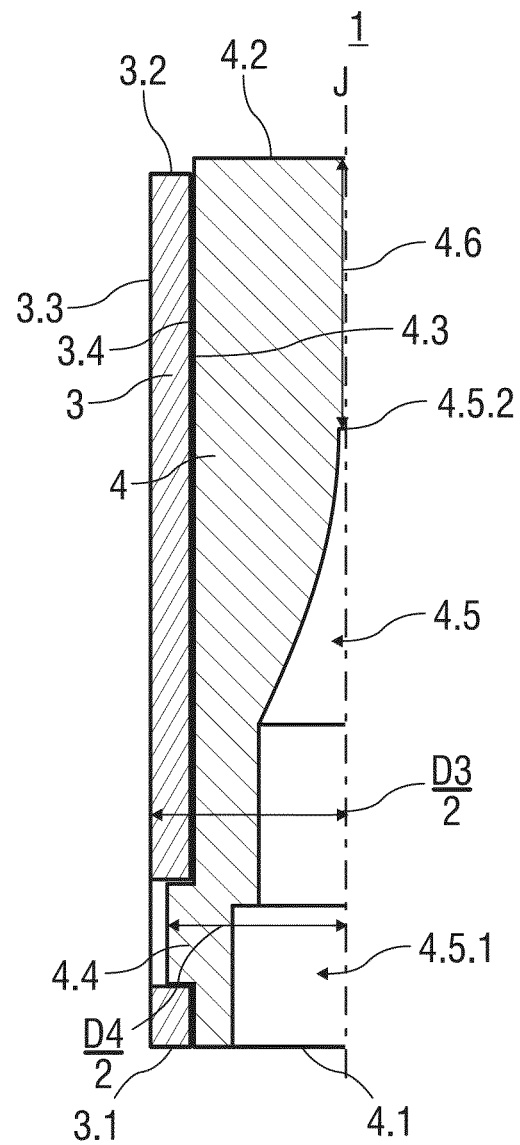
FIG. 6 shows a cross-sectional view of a part of another prior art needle shield assembly.

FIG. 4 shows an exemplary embodiment of a needle shield assembly 1 coupled to a medicament delivery device 2 for use in an injection device according to the present invention. The injection device may be, for example, an auto-injector. In an exemplary embodiment, the injection device comprises a carrier 2.4 adapted to contain a syringe 2.3. The syringe 2.3 includes a needle hub 2.2 at its distal end and a needle 2.1 extending distally from the needle hub 2.2.

When assembling the delivery device 2, the distal end of the syringe 2.3 may be required to pass through an opening 2.4.1 at a distal end 2.4.2 of the carrier 2.4 in an assembly direction 2.5 (e.g., distally relative to the carrier 2.4). In a conventional delivery device 2, a diameter DBH of the opening 2.4.1 may be wide enough to accommodate the diameter of the shoulder 4.4. In the exemplary embodiments of the present invention, because the outer diameter of the outer body 4.4 is substantially equal to the diameter of the inner body 4 at the shoulder 4.4, the distal end of the syringe 2.3 may pass through the opening 2.4.1 of the carrier 2.4 until a shoulder of the syringe 2.3 abuts the distal end 2.4.2 of the carrier 2.4.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A needle shield assembly, comprising:
   an inner body adapted to receive a needle, the inner body comprising a proximal portion having a first outer diameter (D4) and a distal portion having a second outer diameter, wherein the first outer diameter is larger than the second outer diameter,
   an outer body coupled to the inner body, the outer body having a third outer diameter (D3) substantially equal to or less than the first outer diameter, wherein the distal portion of the inner body includes a cap portion having a fourth outer diameter substantially equal to the first outer diameter, the inner body defining an outer surface located between the proximal portion and the cap portion and having a fifth outer diameter less than the fourth outer diameter, and the outer body being coupled to the outer surface of the inner body.

2. The needle shield assembly according to claim 1, wherein the distal portion of the inner body is adapted to frictionally engage the needle.

3. The needle shield assembly according to claim 1, wherein the proximal portion of the inner body is adapted to engage a portion of a medicament delivery device to which the needle is attached.

4. The needle shield assembly according to claim 1, wherein the inner body is constructed of a first material and the outer body is constructed of a second material different from the first material.

5. The needle shield assembly according to claim 4, wherein the first material is a rubber and the second material is a plastic or a harder rubber than the rubber of the first material.

6. The needle shield assembly according to claim 1, wherein an inner surface of the outer body includes one or more projections which engage one or more notches on an outer surface of the inner body.

7. The needle shield assembly according to claim 1, wherein an outer surface of the inner body includes one or more projections which engage one or more notches on an inner surface of the outer body.

8. The needle shield assembly according to claim 6, wherein the projections include a first set of projections having a first geometry and a second set of projections having a second geometry.

9. The needle shield assembly according to claim 1, wherein a distal end of the outer body abuts the cap portion, and a proximal end of the outer body abuts the proximal portion of the inner body.

10. The needle shield assembly according to claim 1, wherein the cap portion is one of an annular projection, a partial annular projection, and one or more radial projections.

* * * * *